(12) United States Patent
Honda et al.

(10) Patent No.: US 11,551,826 B2
(45) Date of Patent: Jan. 10, 2023

(54) METHOD FOR PRODUCING $^{225}$AC

(71) Applicant: NIHON MEDI-PHYSICS CO., LTD., Tokyo (JP)

(72) Inventors: Yoshio Honda, Tokyo (JP); Shinya Yano, Tokyo (JP)

(73) Assignee: NIHON MEDI-PHYSICS CO., LTD., Tokyo (JP)

( * ) Notice: Subject to any disclaimer, the term of this patent is extended or adjusted under 35 U.S.C. 154(b) by 0 days.

(21) Appl. No.: 17/846,398

(22) Filed: Jun. 22, 2022

(65) Prior Publication Data

US 2022/0328207 A1    Oct. 13, 2022

Related U.S. Application Data

(63) Continuation of application No. 17/622,390, filed as application No. PCT/JP2020/025059 on Jun. 25, 2020.

(30) Foreign Application Priority Data

Jul. 2, 2019  (JP) ................................ 2019-123673

(51) Int. Cl.
*G21G 1/10* (2006.01)
*G21G 1/00* (2006.01)
(Continued)

(52) U.S. Cl.
CPC ............. *G21G 1/001* (2013.01); *G21G 1/06* (2013.01); *G21G 1/10* (2013.01); *G21G 1/12* (2013.01); *G21G 2001/0089* (2013.01)

(58) Field of Classification Search
CPC ............ G21G 1/001; G21G 1/06; G21G 1/10; G21G 1/12; G21G 2001/0089
(Continued)

(56) References Cited

U.S. PATENT DOCUMENTS 6,299,666 B1 * 10/2001 Apostolidis .............. G21G 1/10
                                                   376/125
2007/0076834 A1    4/2007 Moreno et al.
(Continued)

FOREIGN PATENT DOCUMENTS

EP          2528063 A2    11/2012
JP      H11-244692 A       9/1999
(Continued)

OTHER PUBLICATIONS

Extended European Search Report dated Aug. 8, 2022, issued for corresponding EP Patent Application No. 20835047.0.
(Continued)

*Primary Examiner* — Jack W Keith
*Assistant Examiner* — Daniel Wasil
(74) *Attorney, Agent, or Firm* — Buchanan, Ingersoll & Rooney PC

(57) ABSTRACT

A method for producing $225^A$ including: a method (X) for purifying a $^{226}$Ra-containing solution, including an adsorption step of allowing a $^{226}$Ra ion to adsorb onto a carrier having a function of selectively adsorbing a divalent cation by bringing a $^{226}$Ra-containing solution into contact with the carrier under an alkaline condition, and an elution step of eluting the $^{226}$Ra ion from the carrier under an acidic condition; a method for producing a $^{226}$Ra target, including an electrodeposition liquid preparation step of preparing an electrodeposition liquid by using a purified $^{226}$Ra-containing solution obtained by the method (X), and an electrodeposition step of electrodepositing a $^{226}$Ra-containing substance on a substrate by using the electrodeposition liquid; and a step of irradiating a $^{226}$Ra target produced by the method for producing a $^{226}$Ra target with at least one selected from a charged particle, a photon, and a neutron by using an accelerator.

9 Claims, 1 Drawing Sheet

(51) Int. Cl.
*G21G 1/06* (2006.01)
*G21G 1/12* (2006.01)

(58) Field of Classification Search
USPC .......................................................... 376/201
See application file for complete search history.

(56) References Cited

U.S. PATENT DOCUMENTS

| | | | |
|---|---|---|---|
| 2009/0101586 A1 | 4/2009 | Brings et al. | |
| 2009/0191122 A1* | 7/2009 | Moreno Bermudez | G21G 1/001 424/1.61 |

FOREIGN PATENT DOCUMENTS

| | | | |
|---|---|---|---|
| JP | H11262661 A | 9/1999 | |
| JP | 2007508531 A | 4/2007 | |
| JP | 2009527731 A | 7/2009 | |
| JP | 2015114315 A | 6/2015 | |

OTHER PUBLICATIONS

Office Action (Request for the Submission of an Opinion) dated Jul. 19, 2022, by Korean Intellectual Property Office in corresponding Korean Patent Application No. 10-2021-7041820 and an English translation of the Office Action. (10 pages).

International Search Report (PCT/ISA/210) with translation and Written Opinion (PCT/ISA/237) dated Sep. 8, 2020, by the Japan Patent Office as the International Searching Authority for International Application No. PCT/JP2020/025059. (11 pages).

Notice of Allowance dated Nov. 14, 2022, by the Korean Patent Office in Korean Patent Application No. 10-2021-7041820 and an English translation of the Notice (5 pages).

* cited by examiner

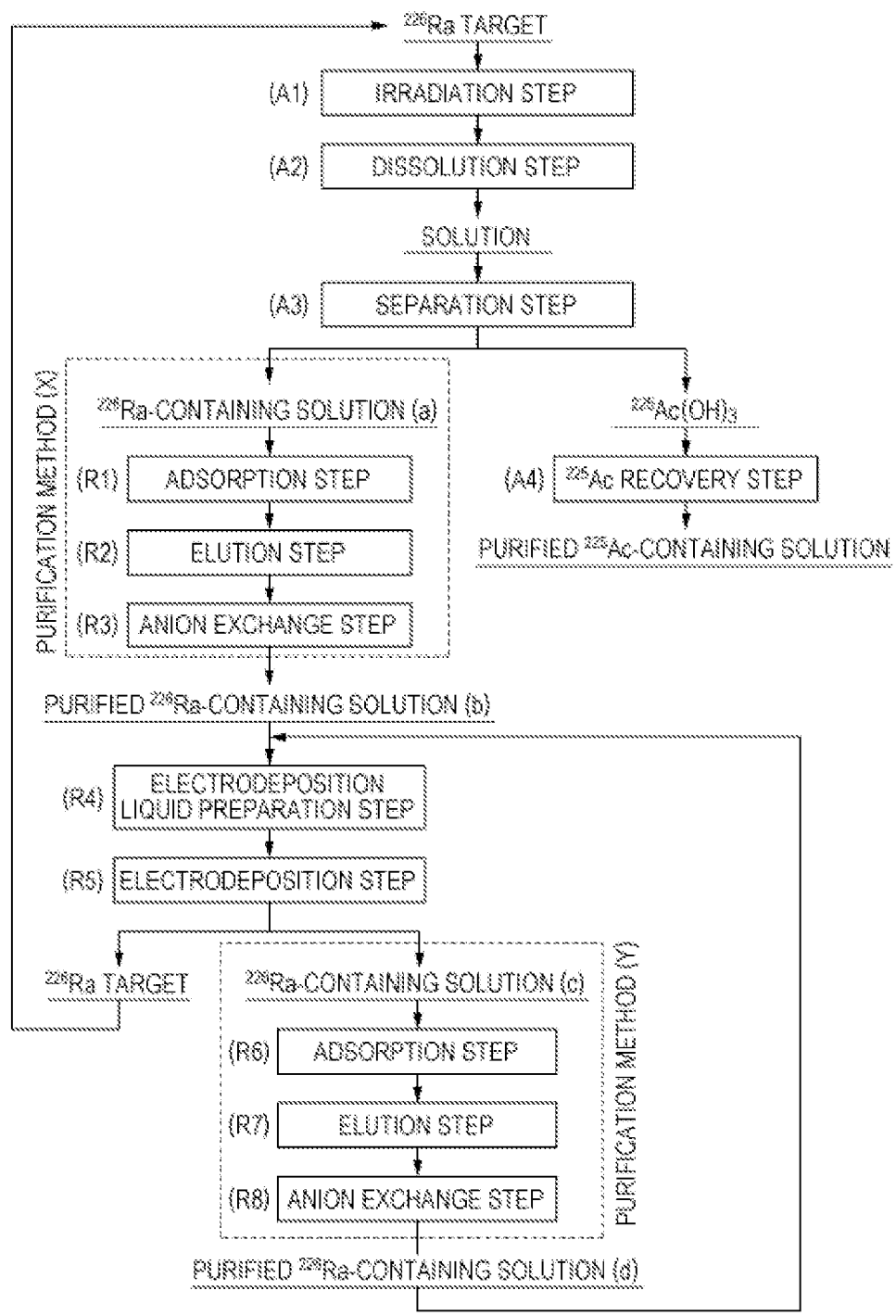

METHOD FOR PRODUCING $^{225}$Ac

CROSS-REFERENCE TO RELATED APPLICATIONS

The present application is a continuation of U.S. patent application Ser. No. 17/622,390, filed on Dec. 23, 2021, which is a national stage application of PCT/JP2020/025059, filed on Jun. 25, 2020, and which claims priority to Japanese Patent Application No. 2019-123673, filed on Jul. 2, 2019, the entire contents of all of which are hereby incorporated by reference.

TECHNICAL FIELD

The present invention relates to a method for purifying a $^{226}$Ra-containing solution, a method for producing a $^{226}$Ra target, and a method for producing $^{225}$Ac.

BACKGROUND ART

In the field of nuclear medicine, radionuclide therapy has been performed in which a drug containing a radioisotope (RI) is selectively taken into a lesion such as a tumor for treatment. Among radiations, an alpha-ray has a characteristic that the effect of unnecessary exposure on the surrounding normal cells is small because the range is short. $^{225}$Ac being one of the alpha-ray emitting nuclides is a radionuclide with a half-life period of 10 days, and has been expected as a therapeutic nuclide in cancer treatment in recent years.

$^{225}$AC is produced by a nuclear reaction of (p, 2n), for example, by irradiating a $^{226}$Ra target with a proton using an accelerator. Patent Literature 1 discloses a method for separation and purification of an $^{225}$AC component from a solution containing $^{226}$Ra ions and $^{225}$AC ions, which is obtained by dissolving the $^{226}$Ra target after irradiation.

CITATION LIST

Patent Literature

Patent Literature 1: JP 2009-527731 A

SUMMARY OF INVENTION

However, there has been a problem that the amount of the $^{225}$AC produced from a $^{226}$Ra target is extremely small, and most of the $^{226}$Ra remains unreacted.

Further, since $^{226}$Ra is a precious nuclide and the disposal of $^{226}$Ra is not easy, it has been demanded to establish a method for purifying efficiently and easily a solution containing $^{226}$Ra ions after $^{225}$AC separation in order to reuse the unreacted $^{226}$Ra. The technique disclosed in Patent Literature 1 has a problem in terms of efficiency and ease, such as the need for distillation and reflux.

The present invention has been made in view of the circumstances as described above, and an object of the present invention is to provide a method for purifying efficiently and easily a $^{226}$Ra-containing solution obtained when $^{225}$Ac is produced from a $^{226}$Ra target, a method for producing a $^{226}$Ra target by using the purified $^{226}$Ra-containing solution obtained by the above purification method, and a method for producing $^{225}$Ac including these above methods.

One embodiment of the present invention is a method for purifying a $^{226}$Ra-containing solution, comprising the steps: (R1) of allowing a $^{226}$Ra ion to adsorb onto a carrier having a function of selectively adsorbing a divalent cation by bringing a $^{226}$Ra-containing solution (a) into contact with the carrier under an alkaline condition; and (R2) of eluting the $^{226}$Ra ions from the carrier under an acidic condition.

Further, another embodiment of the present invention is a method for producing a $^{226}$Ra target, comprising the steps: (R4) of preparing an electrodeposition liquid by using a purified $^{226}$Ra-containing solution (b) obtained by the method for purifying a $^{226}$Ra-containing solution described above; and (R5) of electrodepositing a $^{226}$Ra-containing substance on a substrate by using the electrodeposition liquid.

Furthermore, another embodiment of the present invention is a method for producing $^{225}$Ac, comprising a step (A1) of irradiating a $^{226}$Ra target produced by the method for producing a $^{226}$Ra target described above with at least one kind selected from a charged particle, a photon, and a neutron by using an accelerator to produce $^{225}$Ac.

According to the method for purifying a $^{226}$Ra-containing solution of the present invention, a $^{226}$Ra-containing solution obtained when $^{225}$Ac is produced from a $^{226}$Ra target can be purified efficiently and easily. Further, a $^{226}$Ra target can be produced efficiently by using the purified $^{226}$Ra-containing solution obtained by the above purification method. Furthermore, $^{225}$Ac can be obtained efficiently and stably by a method for producing $^{225}$Ac including these above methods.

BRIEF DESCRIPTION OF DRAWINGS

FIG. 1 is a flow chart showing an outline of the method for purifying a $^{226}$Ra-containing solution, method for producing a $^{226}$Ra target, and method for producing $^{225}$Ac according to the present invention.

DESCRIPTION OF EMBODIMENTS

Hereinafter, the embodiments of the present invention will be described in detail. A flow chart showing an outline of the method for purifying a $^{226}$Ra-containing solution, method for producing a $^{226}$Ra target, and method for producing $^{225}$Ac according to the present invention is shown in FIG. 1.

Method for Purifying $^{226}$Ra-Containing Solution The method for purifying a $^{226}$Ra-containing solution (hereinafter, also referred to as "purification method (X)") according to the present invention is characterized by including: an adsorption step (R1) of allowing a $^{226}$Ra ion to adsorb onto a carrier having a function of selectively adsorbing a divalent cation (hereinafter, also referred to as "carrier (i)") by bringing a $^{226}$Ra-containing solution (a) into contact with the carrier (i) under an alkaline condition; and an elution step (R2) of eluting the $^{226}$Ra ions from the carrier (i) under an acidic condition. In this way, $^{226}$Ra ions are concentrated, and impurities can be reduced. The solution obtained by the purification method (X) is referred to as a purified $^{226}$Ra-containing solution (b).

The $^{226}$Ra-containing solution (a) is not particularly limited as long as it is a solution containing $^{226}$Ra ions, and is preferably an aqueous solution containing $^{226}$Ra ions. In order to perform an adsorption step (R1) under an alkaline condition, the $^{226}$Ra-containing solution (a) is preferably an alkaline aqueous solution, and has a pH of preferably 8 or more, and more preferably 9 or more. Examples of the alkaline aqueous solution include an aqueous ammonium solution, an aqueous sodium hydroxide solution, and an aqueous potassium hydroxide solution. In this way, $^{226}$Ra ions can be adsorbed onto a carrier (i) efficiently.

As the $^{226}$Ra-containing solution (a), a solution after an irradiation step (A1), a dissolution step (A2), and a separation step (A3) in the production method for producing $^{225}$Ac to be described later, that is, a solution obtained by separating an $^{225}$Ac component from a solution in which a $^{226}$Ra target irradiated with at least one kind selected from a charged particle, a photon, and a neutron by using an accelerator has been dissolved may be used.

Adsorption Step (R1)

In an adsorption step (R1), $^{226}$Ra ions are adsorbed onto a carrier (i) by bringing a $^{226}$Ra-containing solution (a) into contact with the carrier (i) under an alkaline condition.

The carrier (i) is not particularly limited as long as it can form a complex with a metal ion under an alkaline condition and elute the metal ion under an acidic condition. As the carrier (i), for example, a carrier having a divalent cation-exchange group can be mentioned. As the divalent cation-exchange group, specifically, an iminodiacetic acid group, a polyamine group, or a methyl glycan group can be mentioned. As the divalent cation-exchange group, an iminodiacetic acid group is preferable.

The carrier having a divalent cation-exchange group is not particularly limited as long as the divalent cation-exchange group is retained on a solid-phase carrier such as a resin. A more preferable example of the carrier includes a styrene-divinylbenzene copolymer retaining an iminodiacetic acid group. Examples of the commercially available resin having an iminodiacetic acid group include the "Chelex" series manufactured by Bio-Rad Laboratories, Inc., "DIAION" series manufactured by Mitsubishi Chemical Corporation, and "Amberlite" series manufactured by The Dow Chemical Company, and more specifically include "Chelex 100" (particle diameter: 50 to 100 mesh, and ionic form: Na form, Fe form) manufactured by Bio-Rad Laboratories, Inc. The carrier (i) may be charged in a tube for use. The tube is not particularly limited as long as the carrier (i) can be charged in the tube and the tube has flexibility, and is preferably a flexible tube made of rubber, a resin, or the like, and more preferably a tube for medical use.

By using such a tube, a length longer than that of a common glass column can be obtained, that is, the number of theoretical plates can be increased, so that the adsorption efficiency of $^{226}$Ra ions can be increased. Further, the carrier (i) through which a radioactive substance ($^{226}$R-containing solution) has been passed can be easily discarded while being charged in a tube without radioactively contaminating other instruments, devices, and the like.

Elution Step (R2)

In an elution step (R2), $^{226}$Ra ions are eluted from a carrier (i) under an acidic condition. Specifically, by passing an inorganic acid through the carrier (i), the $^{226}$Ra ions adsorbed onto the carrier (i) can be eluted.

The inorganic acid is not particularly limited as long as it can dissolve a $^{226}$Ra component adsorbed onto the carrier (i) and generate ions, and examples of the inorganic acid include hydrochloric acid and nitric acid.

In this regard, from the viewpoints that $^{226}$Ra ions can be efficiently eluted from the carrier and that anions derived from an inorganic acid can be efficiently removed in the later step, the concentration of the inorganic acid is preferably 0.1 to 12 mol/L, more preferably 0.3 to 5 mol/L, furthermore preferably 0.5 to 2 mol/L, and particularly preferably 0.7 to 1.5 mol/L.

Anion Exchange Step (R3)

The purification method (X) according to the present invention may further include an anion exchange step (R3) in which a solution containing $^{226}$Ra ions eluted in an elution step (R3) is passed through an anion exchange resin.

If any anions (for example, chloride ions or the like) derived from an inorganic acid (for example, hydrochloric acid or the like) used in the elution step (R2) remain in the solution, such anions may affect the electrodeposition rate of $^{226}$Ra ions in an electrodeposition step (R5) described later. For this reason, it is preferable to treat the solution containing the $^{226}$Ra ions eluted in the elution step (R2), in the anion exchange step (R3) because the anions derived from an inorganic acid can be reduced by being exchanged for hydroxide ions, and the electrodeposition efficiency of $^{226}$Ra ions in the electrodeposition step (R5) can be improved.

The anion exchange resin is not particularly limited as long as it can exchange anions (for example, chloride ions or the like) derived from an inorganic acid for hydroxide ions, and is preferably a strongly basic anion exchange resin, and more preferably a resin having a quaternary ammonium salt. Examples of the commercially available anion exchange resin include the "MONOSPHERE" series manufactured by The Dow Chemical Company, and the "AG" series manufactured by Bio-Rad Laboratories, Inc., and more specifically include "MONOSPHERE 550A" (particle diameter: 590±50 mesh, ionic form: OH form).

In this regard, the anion exchange resin may be charged in a tube for use in a similar manner as in the case of a carrier (i). As the tube capable of being used for the charging, a tube similar to that in which the above-described carrier (i) is to be charged can be mentioned.

Other Step

A step of washing a carrier (i) may be included between the step (R1) and the step (R2) in a purification method (X). Specifically, a step can be mentioned in which water is passed through a carrier (i). In this way, the proportion of impurities contained in a purified $^{226}$Ra-containing solution (b) can be reduced.

Method for Producing $^{226}$Ra Target The method for producing a $^{226}$Ra target according to the present invention is characterized by including an electrodeposition liquid preparation step (R4) of preparing an electrodeposition liquid by using a purified 226Ra-containing solution (b) obtained by a purification method (X), and an electrodeposition step (R5) of electrodepositing a $^{226}$Ra-containing substance on a substrate by using the electrodeposition liquid.

It is preferable that the method for producing a $^{226}$Ra target according to the present invention further includes a purification method (hereinafter, also referred to as "purification method (Y)") including an adsorption step (R6) of allowing $^{226}$Ra ions to adsorb onto a carrier having a function of selectively adsorbing divalent cations (hereinafter, also referred to as "carrier (ii)") by bringing a $^{226}$Ra-containing solution (c) after the electrodeposition step (R5) into contact with the carrier (ii) under an alkaline condition, and an elution step (R7) of eluting the $^{226}$Ra ions from the carrier (ii) under an acidic condition. The solution obtained by the purification method (Y) is referred to as a purified $^{226}$Ra-containing solution (d).

Electrodeposition Liquid Preparation Step (R4)

In an electrodeposition liquid preparation step (R4), an electrodeposition liquid is prepared by using a purified $^{226}$Ra-containing solution (b), and at this time, a purified $^{226}$Ra-containing solution (d) obtained by a purification method (Y) may be mixed with the purified $^{226}$Ra-containing solution (b) to prepare an electrodeposition liquid. In this way, the recovery rate of $^{226}$Ra can be further increased, and $^{226}$Ra can be recovered more efficiently.

By adding as needed a buffer agent, an acid, or the like to a purified $^{226}$Ra-containing solution (b) or a mixture of a purified $^{226}$Ra-containing solution (b) and a purified $^{226}$Ra-containing solution (d), an electrodeposition liquid to be used in an electrodeposition step (R5) described later can be prepared.

Examples of the buffer agent include a chloride salt such as ammonium chloride; a carbonate such as ammonium carbonate, sodium carbonate, potassium carbonate, calcium carbonate, or magnesium carbonate; a hydrogen carbonate such as ammonium hydrogen carbonate, sodium hydrogen carbonate, or potassium hydrogen carbonate; an acetate such as ammonium acetate, sodium acetate, or potassium acetate; a succinate such as monosodium succinate, disodium succinate, monopotassium succinate, dipotassium succinate, monoammonium succinate, or diammonium succinate; and a benzoate such as sodium benzoate, potassium benzoate, or ammonium benzoate. Among them, ammonium acetate is preferable from the viewpoints, for example, of being easy to maintain the pH of an electrodeposition liquid within the desired range described later, and of electrodepositing $^{226}$Ra ions on a substrate more efficiently.

Examples of the acid include an inorganic acid, and a carboxylic acid having 2 to 6 carbon atoms. Examples of the inorganic acid include nitric acid, hydrochloric acid, and boric acid. Further, examples of the carboxylic acid having 2 to 6 carbon atoms include acetic acid, succinic acid, and benzoic acid.

The acid is preferably a monovalent or divalent acid from the viewpoint of improving the yield of $^{225}$Ac.

From the viewpoint that $^{226}$Ra ions can be more efficiently electrodeposited on a substrate, the pH of an electrodeposition liquid is preferably 4 to 7, and more preferably 5 to 6. The pH of the electrodeposition liquid can be kept within the above range by appropriately adding a buffer agent or an acid.

The electrodeposition liquid may contain as needed a component that has been used in conventional electroplating or the like within a range that does not impair the effects of the present invention. As the other components, one kind may be used, or two or more kinds may be used.

Electrodeposition Step (R5)

In an electrodeposition step (R5), a $^{226}$Ra-containing substance is electrodeposited on a substrate by using an electrodeposition liquid prepared in an electrodeposition liquid preparation step (R4).

Examples of the $^{226}$Ra-containing substance include a $^{226}$Ra metal, and a $^{226}$Ra salt. The obtained $^{226}$Ra target can be reused in an irradiation step (A1) in a method for producing $^{225}$Ac described later.

Examples of the metal to be used for the substrate include aluminum, copper, titanium, silver, gold, iron, nickel, niobium, and alloys containing these metals (such as phosphor bronze, brass, nickel silver, beryllium copper, Corson alloy, and stainless steel).

Further, the substrate may be plated a conductive support with these metals.

As the substrate, a gold plate is preferable, for example, from the viewpoint of being less likely to cause adverse effects on an accelerator and the like even during irradiation with at least one kind selected from a charged particle, a photon, and a neutron by using the accelerator and of being capable of preventing contamination with a metal derived from the substrate during the irradiation or the dissolution of a target, and from the viewpoint of being capable of electrodepositing $^{226}$Ra ions on a substrate more efficiently.

The electrodeposition step (R5) can be performed by a known method. Specifically, by energizing an electrodeposition liquid, a $^{226}$Ra-containing substance is electrodeposited on a substrate.

As the power source for energization, it is not particularly limited, and a direct current (DC) power source, an alternating current (AC) power source, a pulse power source, a PR pulse power source, or the like can be used. Among them, a pulse power source or a PR pulse power source is preferably used, for example, from the viewpoints of being easy to improve the diffusion of $^{226}$Ra ions and to uniformly electrodeposit a $^{226}$Ra-containing substance, being capable of suppressing the generation of heat, and being capable of performing the electrodeposition with a small power source.

As the temperature (temperature of electrodeposition liquid) in the electrodeposition step (R5), it is not particularly limited, and a temperature of, for example, around 10 to 80° C. can be employed.

Adsorption Step (R6)

In an adsorption step (R6), $^{226}$Ra ions are allowed to adsorb onto a carrier (ii) by bringing a $^{226}$Ra-containing solution (c) containing residual $^{226}$Ra ions after an electrodeposition step (R5) into contact with the carrier (ii) under an alkaline condition.

As the carrier (ii), a carrier similar to the carrier (i) to be used in an adsorption step (R1) in a purification method (X) can be used, and the carrier (ii) may be charged in a tube for use in a similar manner as in the case of the purification method (X).

Elution Step (R7)

In an elution step (R7), $^{226}$Ra ions are eluted from a carrier (ii) under an acidic condition. Specifically, by passing an inorganic acid through the carrier (ii), the $^{226}$Ra ions adsorbed onto the carrier (ii) can be eluted.

As the inorganic acid to be used in the elution step (R7), an inorganic acid similar to that to be used in an elution step (R2) can be used, and the inorganic acid can also have a concentration similar to that of the inorganic acid to be used in the elution step (R2).

Anion Exchange Step (R8)

A purification method (Y) may further include an anion exchange step (R8) in which a solution containing $^{226}$Ra ions eluted in an elution step (R7) is passed through an anion exchange resin.

If any anions (for example, chloride ions or the like) derived from an inorganic acid (for example, hydrochloric acid or the like) used in the elution step (R7) remain in the solution, such anions may affect the electrodeposition efficiency of $^{226}$Ra ions when an electrodeposition liquid is prepared in an electrodeposition liquid preparation step (R4) and then an electrodeposition step (R4) is performed. For this reason, it is preferable to treat a solution containing the $^{226}$Ra ions eluted in the elution step (R7), in an anion exchange step (R8) because the anions derived from an inorganic acid can be reduced by being exchanged for hydroxide ions, and the electrodeposition rate of the $^{226}$Ra ions can be improved in a case where the solution is used again as an electrodeposition liquid in the electrodeposition step (R4).

Other Step

A step of washing a carrier (ii) may be included between the step (R6) and the step (R7) in a purification method (Y). Specifically, a step can be mentioned in which water is passed through a carrier (ii). In this way, the proportion of impurities contained in a purified $^{226}$Ra-containing solution (d) is reduced.

Method for Producing $^{225}$Ac

The method for producing $^{225}$Ac according to the present invention is characterized by including an irradiation step (A1) of irradiating a $^{226}$Ra target produced by the above-described method for producing a $^{226}$Ra target according to the present invention with at least one kind selected from a charged particle, a photon, and a neutron by using an accelerator. It is preferable that the method for producing $^{225}$Ac according to the present invention further includes a dissolution step (2) of dissolving the $^{226}$Ra target irradiated in the irradiation step (A1), and a separation step (A3) of separating a colloidal $^{225}$Ac component by alkalizing the solution obtained in the dissolution step (A2).

Irradiation Step (A1)

In an irradiation step (A1), a $^{226}$Ra target produced by the above-described method for producing a $^{226}$Ra target according to the present invention is irradiated with at least one kind selected from a charged particle, a photon, and a neutron by using an accelerator, and $^{225}$Ac is allowed to generate by a nuclear reaction. As the particle, a proton, a deuteron, an α particle, or a γ particle is preferable, and a proton is more preferable.

In this regard, as for the irradiation method and the irradiation condition, a known method and a known condition can be adopted.

Dissolution Step (A2)

In a dissolution step (A2), a $^{226}$Ra target irradiated in an irradiation step (A1) is dissolved in an acid solution. As a result, a solution containing $^{226}$Ra ions and $^{225}$Ac ions is obtained.

As the acid solution, an acid solution that can dissolve $^{225}$Ac and $^{226}$Ra as ions is mentioned, and specifically an aqueous solution of an inorganic acid such as hydrochloric acid, or nitric acid, preferably an aqueous solution of hydrochloric acid is mentioned.

Separation Step (A3)

In a separation step (A3), a colloidal $^{225}$Ac component by alkalizing a solution obtained in a dissolution step (A2) is separated.

The $^{225}$Ac dissolved in water as $^{225}$Ac ions under an acidic condition becomes actinium hydroxide $^{225}$Ac (OH)$_3$) under an alkaline condition, and forms colloids in an aqueous solution. The colloidal actinium hydroxide is collected on a filter by filtering with a membrane filter or the like, and can be separated from the solution.

In addition, a $^{226}$Ra component exists as ions in a solution to which an alkaline solution has been added, and is separated from an $^{225}$Ac component by a separation step (A3), and a $^{226}$Ra-containing solution (a) is obtained. The obtained $^{226}$Ra-containing solution (a) is supplied to an adsorption step (R1) in a purification method (X).

Recovery Step (A4)

By dissolving $^{225}$Ac separated in a separation step (A3) with an acid solution, an $^{225}$Ac-containing solution is obtained. The obtained $^{225}$Ac-containing solution may be further purified by a known method, as needed.

Dissolution

Actinium hydroxide separated in a separation step (A3) can be dissolved by using an acid solution. The acid solution to be used for dissolution is not particularly limited as long as it can dissolve actinium hydroxide as ions, and for example, the same acid solution as that used in a dissolution step (A2) can be used. Further, it is preferable that the concentration is 1 to 6 mol/L, and more preferably 2 to 5 mol/L, from the viewpoints that actinium hydroxide is easily dissolved as ions and that a carrier easily adsorbs $^{226}$Ra.

Purification

A solution containing $^{225}$Ac ions dissolved with an acid solution can be purified, for example, by a solid-phase extraction method. A solid-phase extraction agent to be used in the solid-phase extraction method is not particularly limited as long as it can capture $^{225}$Ac ions and then elute the $^{225}$Ac ions under a predetermined condition, and examples of the solid-phase extraction agent include ones containing a compound represented by the formula (1).

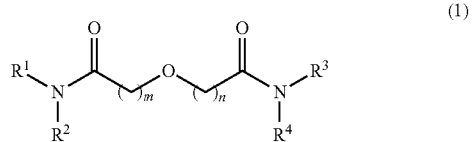

(1)

In the formula (1), m and n are independently 0 or 1, and preferably 1; and $R^1$, $R^2$, $R^3$, and $R^4$ are independently a straight or branched chain alkyl group having 8 or more and 12 or less carbon atoms, and preferably independently an octyl group or 2-ethylhexyl. Such a solid-phase extraction agent is commercially available, for example, as "DGA Resin" manufactured by Eichrom Technologies Inc.

As the specific purification method, first, an $^{225}$Ac-containing solution is passed through a solid-phase extraction agent to capture $^{225}$Ac ions and the like in the solid-phase extraction agent. Next, the captured unnecessary $^{226}$Ra is eluted by passing the solution through a solid-phase extraction agent with an inorganic acid such as hydrochloric acid. At this time, the concentration of the inorganic acid is set to a relatively high concentration so that $^{225}$Ac does not elute. After that, $^{225}$Ac ions can be eluted from the solid-phase extraction agent by passing through an inorganic acid having a relatively low concentration.

EXAMPLES

Hereinafter, the present invention is further specifically described on the basis of Examples, however, the present invention is in no way limited to these Examples.

Examples 1 and 2

Evaluation Item 1: Mass Balance of $^{226}$Ra in Purification Method (X)

An irradiated $^{226}$Ra target (size: 010 mm, thickness: 2 to 3 mm, and $^{226}$Ra mass: 0.3 to 1 mg) was dissolved in 5 mL of 1 mol/L hydrochloric acid, and then the obtained solution was filtered with a membrane filter to remove insoluble matters. To the filtrate, 1 mL of 28% by mass ammonia water (product name: Ammonia solution (25.0 to 27.9%) for atomic absorption spectrometry, manufactured by KANTO CHEMICAL CO., INC.) was added to adjust the pH to 10 to 12, and colloid of actinium hydroxide was generated. Next, the generated actinium hydroxide was filtered by using a membrane filter at a flow rate of 1 to 2 mL/min to recover a $^{226}$Ra-containing solution (a-1). The radioactivity of the obtained $^{226}$Ra-containing solution (a-1) was measured by a germanium semiconductor detector manufactured by EURISYS MESURES.

Next, in order to prevent contamination by Na in a purified $^{226}$Ra-containing solution (b-1) described later, one that had been obtained by converting Chelex 100 (particle diameter: 50 to 100 mesh, ionic form: Na form, and use amount: 3 mL, manufactured by Bio-Rad Laboratories, Inc.) to a $NH_4^+$ form was charged in a medical tube having an inner diameter of 3.2 mm, an outer diameter of 4.4 mm, and a length of 50 cm (extension tube, 3.2×4.4×500 mm (4 mL), MS-FL, manufactured by HAKKO CO., LTD.), 50 to 80 mL of the obtained $^{226}$Ra-containing solution (a-1) (pH >9) was passed through the medical tube at a flow rate of 1 to 2 mL/min, and the eluate was taken as a waste liquid (W1). Next, 10 mL of water was passed through Chelex 100 at a flow rate of 1 to 2 mL/min, and the eluate was merged with the waste liquid (W1).

Next, MONOSPHERE 550A (particle diameter: 590 ±50 mesh, ionic form: OH form, and use amount: 20 mL, manufactured by The Dow Chemical Company) was washed with hydrochloric acid, water, sodium hydroxide, and water in this order, and then the washed MONOSPHERE 550A was charged in a medical tube having an inner diameter of 3.2 mm, an outer diameter of 4.4 mm, and a length of 200 cm (extension tube, 3.2×4.4×500 mm (4 mL), MS-FL, manufactured by HAKKO CO., LTD.), and the medical tube was connected to a tube filled with Chelex 100. 10 mL of 1 mol/L hydrochloric acid was passed through Chelex 100 and MONOSPHERE 550A in this order at a flow rate of 1 to 2 mL/min, and then 8 mL of water was further passed through the resultant Chelex 100 and MONOSPHERE 550A at a flow rate of 1 to 2 mL/min, and 18 mL of a purified $^{226}$Ra-containing solution (b-1) was obtained.

The radioactivity of the obtained purified $^{226}$Ra-containing solution (b-1) was measured by a germanium semiconductor detector. Further, the radioactivity of each of the waste liquid (W1) and the materials of Chelex and MONOSPHERE 550A was measured in order to examine the distribution of residual $^{226}$Ra.

The same operation was performed twice in total (Examples 1 and 2), and the mass balance of each $^{226}$Ra was calculated. The results are shown in Table 1.

TABLE 1

|  | Example 1 | | Example 2 | |
| --- | --- | --- | --- | --- |
|  | Numerical value | Percentage | Numerical value | Percentage |
| $^{226}$Ra-Containing solution (a-1) (calculated value) | 9.13 MBq | 100% | 2.97 MBq | 100% |
| Waste liquid (W1) | N.D | <0.2%*1 | N.D | <0.7%*1 |
| Residual in material Chelex after elution | N.D | <0.2%*1 | N.D | <0.7%*1 |
| Residual in material MONOSPHERE 550A after elution | N.D | <0.2%*1 | N.D | <0.7%*1 |
| Purified $^{226}$Ra-containing solution (b-1) | 9.13 MBq | >99.3% | 2.97 MBq | >98.0% |

In Table 1, the $^{226}$Ra-containing solution (a-1) was calculated from the following formula (1).

$^{226}$Ra (calculation value) of $^{226}$Ra-containing solution (a-1)=purified $^{226}$Ra-containing solution (b-1)+residual $^{226}$Ra in Chelex 100+residual $^{226}$Ra in MONOSPHERE 550A+waste liquid (W1) . . . (1)

In this regard, for the purified $^{226}$Ra-containing solution (b-1) of Example 2, a value calculated from the difference in radioactivity between the Ra-adsorbed Chelex and the Ra-eluted Chelex was used.

The values with *1 shown in Table 1 were calculated assuming that a maximum of 0.02 MBq was detected because it is unclear whether the measurement of less than 0.02 MBq is possible although the measured value was N.D.

As in Examples 1 and 2, by passing the $^{226}$Ra-containing solution (a-1) through Chelex 100, impurities (ammonium chloride (hydrochloric acid+ammonia), ammonia, and the like) other than $^{226}$Ra can be removed. Further, most of the chloride ions can be removed by these adsorption step (R1), elution step (R2), and anion exchange step (R3).

Examples 3 to 8

Evaluation Item 2: Mass Balance of $^{226}$Ra after Dissolution Step (A2) and Separation Step (A3)

An irradiated $^{226}$Ra target (size: Φ10 mm, thickness: 2 to 3 mm, and $^{226}$Ra mass: 0.3 to 1 mg) was dissolved in 5 mL of 1 mol/L hydrochloric acid, and then the obtained solution was filtered with a membrane filter to remove insoluble matters. To the filtrate, 1 mL of 28% by mass ammonia water (product name: Ammonia solution (25.0 to 27.9%) for atomic absorption spectrometry, manufactured by KANTO CHEMICAL CO., INC.) was added to adjust the pH to 10 to 12, and colloid of actinium hydroxide was generated. Next, the generated actinium hydroxide was filtered by using a membrane filter at a flow rate of 1 to 2 mL/min to obtain a $^{226}$Ra-containing solution (a-2).

Next, DGA Resin (DGA Normal Resin, 1-mL cartridge, manufactured by Eichrom Technologies Inc.) was connected to a membrane filter. 6 mL of 4 mol/L nitric acid was passed through the membrane filter and the DGA Resin in this order at a flow rate of 1 to 2 mL/min, and the eluate was taken as a waste liquid (W2).

The radioactivity of the solution after the dissolution step (A2) was measured by a germanium semiconductor detector. Further, the radioactivity of each of the waste liquid (W2) and the materials of membrane filter and DGA Resin was measured by a germanium semiconductor detector in order to examine the distribution of residual $^{226}$Ra. The same operation was performed three times in total (Examples 3 to 5), and the mass balance of each $^{226}$Ra was calculated. The results are shown in Table 2.

Evaluation Item 3: Mass Balance of $^{225}$Ac

Next, the DGA Resin was removed from the membrane filter, 6 mL of 8 mol/L hydrochloric acid was passed through the DGA Resin at a flow rate of 1 to 2 mL/min, and the eluate was taken as a waste liquid (W3). After that, 10 mL of 0.01 mol/L hydrochloric acid was passed through the DGA Resin at a flow rate of 1 to 2 mL/min, and an $^{225}$Ac-containing solution was obtained.

The radioactivity of the obtained $^{225}$Ac-containing solution was measured by a germanium semiconductor detector. Further, the radioactivity of each of the waste liquid (W3) and the materials of membrane filter and DGA Resin was measured by a germanium semiconductor detector in order to examine the distribution of residual $^{225}$Ac. The same operation was performed three times in total (Examples 6 to 8), and the results are shown in Table 3.

The values with *1 shown in Table 2 were calculated assuming that a maximum of 0.02 MBq was detected because it is unclear whether the measurement of less than 0.02 MBq is possible although the measured value was N.D.

The $^{226}$Ra-containing solution (a-2) not containing the waste liquid (W2) after the separation step (A3) in Table 2 was calculated from the following formula (2).

$^{226}$Ra-containing solution (a-2) not containing waste liquid (W2) (calculation value) =$^{226}$Ra contained in the solution after dissolution step (A2)—residual $^{226}$Ra in the material after separation step (A3) (membrane filter)—residual $^{226}$Ra in the material after separation step (A3) (DGA Resin) —$^{226}$Ra amount of the waste liquid (W2) after separation step (A3) . . . (2)

The amount of $^{226}$Ra contained in the solution after the dissolution step (A2) was calculated by collecting a part of the solution, measuring the amount of the part, and converting the measured amount of the part to an amount for the entire solution.

The values with *1 shown in Table 3 were calculated assuming that a maximum of 0.58 kBq was detected because it is unclear whether the measurement of less than 0.58 kBq is possible although the measured value was N.D.

The values with *2 shown in Table 3 were used to calculate the $^{225}$Ac membrane filter-collected amount after the separation step (A3).

TABLE 2

|  |  | Example 3 | | Example 4 | | Example 5 | |
| --- | --- | --- | --- | --- | --- | --- | --- |
|  |  | Numerical value | Percentage | Numerical value | Percentage | Numerical value | Percentage |
| Solution after dissolution step (A2) | | 11.70 MBq | 100% | 17.03 MBq | 100% | 35.90 MBq | 100% |
| Residual in material | Membrane filter | N.D | <0.2%*1 | N.D | <0.1%*1 | 0.02 MBq | 0.1% |
|  | DGA Resin | N.D | <0.2%*1 | N.D | <0.1%*1 | N.D | <0.1%*1 |
| Waste liquid (W2) | | 0.18 MBq | 1.5% | 0.03 MBq | 0.2% | 0.46 MBq | 1.3% |
| Recovered amount | $^{226}$Ra-Containing solution (a-2) not containing waste liquid (W2) (calculated value) | 11.52 MBq | >98.1% | 17.00 MBq | >99.6% | 35.43 MBq | >98.6% |
|  | $^{226}$Ra-Containing solution (a-2) containing waste liquid (W2) (calculated value) | 11.70 MBq | >98.7% | 17.03 MBq | >99.8% | 35.88 MBq | >99.9% |

TABLE 3

|  |  | Example 6 | | Example 7 | | Example 8 | |
| --- | --- | --- | --- | --- | --- | --- | --- |
|  |  | Numerical value | Percentage | Numerical value | Percentage | Numerical value | Percentage |
| Membrane filter-collected amount (calculated value) | | 49.30 kBq | 100% | 47.55 kBq | 100% | 73.45 kBq | 100% |
| Residual in material | Membrane filter*2 | N.D | <1.2%*1 | N.D | <1.2%*1 | 0.93 kBq | 1.27% |
|  | DGA Resin*2 | N.D | <1.2%*1 | N.D | <1.2%*1 | N.D | <0.8%*1 |
| Waste liquid (W3) after passed through DGA Resin*2 | | N.D | <1.2%*1 | 1.67 kBq | 3.50% | N.D | <0.8%*1 |
| Recovered amount | After membrane collection*2 | 49.30 kBq | >96.5%*3 | 45.88 kBq | >94.1%*3 | 72.51 kBq | >97.1%*3 |

The values of the membrane filter-collected amount shown in Table 3 were calculated from the following calculation formula (3).

Membrane filter-collected amount (calculation value) after separation step (A3)=residual $^{225}$Ac in the material after $^{225}$Ac recovery step (A4) (membrane filter)+residual $^{225}$Ac in the material after $^{225}$Ac recovery step (A4) (DGA Resin) +$^{225}$Ac amount of the waste liquid (W3) after being passed through DGA Resin of $^{225}$Ac recovery step (A4) $^{225}$Ac recovered amount in purified $^{225}$Ac-containing solution (3)

In this regard, as the $^{225}$Ac recovered amount in the purified $^{225}$Ac-containing solution of Example 6, a value calculated from the difference in radioactivity between the Ac adsorbed-DGA and the Ac-eluted DGA was used.

The values with *3 shown in Table 3 are each the mass balance after collection by a membrane filter, and the uncollected matters by the membrane filter are not taken into consideration. Further, since the radioactivity of $^{225}$Ac in the $^{226}$Ra solutions before and after being passed through a membrane filter cannot be measured due to the influence of $^{226}$Ra, the recovery rate was calculated by assuming the denominator as "the membrane filter-collected amount after separation step (A3) (calculation value)".

The invention claimed is:

1. A method for producing $^{225}$Ac, comprising:
   a method (X) for purifying a $^{226}$Ra-containing solution, comprising an adsorption step (R1) of allowing a $^{226}$Ra ion to adsorb onto a resin carrier having a function of selectively adsorbing a divalent cation by bringing a 226Ra-containing solution (a) into contact with the carrier under an alkaline condition, and an elution step (R2) of eluting the $^{226}$Ra ion from the carrier under an acidic condition;
   a method for producing a $^{226}$Ra target, comprising an electrodeposition liquid preparation step (R4) of preparing an electrodeposition liquid by using a purified $^{226}$Ra-containing solution (b) obtained by the method (X), and an electrodeposition step (R5) of electrodepositing a $^{226}$Ra-containing substance on a substrate by using the electrodeposition liquid; and
   a step (A1) of irradiating a $^{226}$Ra target produced by the method for producing a $^{226}$Ra target with at least one kind selected from a charged particle, a photon, and a neutron by using an accelerator to produce $^{225}$Ac.

2. The method for producing $^{225}$Ac according to claim 1, wherein
   the carrier has a divalent cation-exchange group.

3. The method for producing $^{225}$Ac according to claim 1, wherein
   the carrier has an iminodiacetic acid group.

4. The method for producing $^{225}$Ac according to claim 1, the method (X) further comprises a step (R3) of performing anion exchange by passing a solution containing a $^{226}$Ra ion eluted in the elution step (R2) through an anion exchange resin.

5. The method for producing $^{225}$Ac according to claim 1, wherein
   the $^{226}$Ra-containing solution (a) is obtained by separating an $^{225}$Ac component from a solution in which a $^{226}$Ra target irradiated with at least one kind selected from a charged particle, a photon, and a neutron by using an accelerator has been dissolved.

6. The method for producing $^{225}$Ac according to claim 1, wherein
   the carrier is charged in a tube.

7. The method for producing $^{225}$Ac according to claim 1, further comprising
   a purification method (Y) comprising the steps:
   (R6) of allowing a $^{226}$Ra ion to adsorb onto a carrier having a function of selectively adsorbing a divalent cation by bringing a $^{226}$Ra-containing solution (c) after the electrodeposition step (R5) into contact with the carrier under an alkaline condition; and
   (R7) of eluting the $^{226}$Ra ion from the carrier under an acidic condition, wherein
   a purified $^{226}$Ra-containing solution (d) obtained by the purification method (Y) is mixed with the purified $^{226}$Ra-containing solution (b), and an electrodeposition liquid is prepared in the electrodeposition liquid preparation step (R4).

8. The method for producing $^{225}$Ac according to claim 7, the purification method (Y) further comprises a step
   (R8) of performing anion exchange by passing a solution containing a $^{226}$Ra ion eluted in the elution step (R7) through an anion exchange resin.

9. The method for producing $^{225}$Ac according to claim 1, further comprising the steps:
   (A2) of dissolving the $^{226}$Ra target irradiated in the irradiation step (A1); and
   (A3) of separating a colloidal $^{225}$Ac component by alkalizing the solution obtained in the dissolution step (A2).

* * * * *